(12) United States Patent
Schaub et al.

(10) Patent No.: US 9,029,605 B2
(45) Date of Patent: May 12, 2015

(54) METHOD FOR PREPARING MENTHONE FROM ISOPULEGOL

(71) Applicant: BASF SE, Ludwigshafen (DE)

(72) Inventors: Thomas Schaub, Neustadt (DE); Martine Weis, Mannheim (DE); Stefan Rüdenauer, Worms (DE)

(73) Assignee: BASF SE (DE)

( * ) Notice: Subject to any disclaimer, the term of this patent is extended or adjusted under 35 U.S.C. 154(b) by 0 days.

(21) Appl. No.: 14/022,396

(22) Filed: Sep. 10, 2013

(65) Prior Publication Data

US 2014/0073817 A1    Mar. 13, 2014

Related U.S. Application Data

(60) Provisional application No. 61/698,745, filed on Sep. 10, 2012.

(51) Int. Cl.
*C07C 45/00* (2006.01)

(52) U.S. Cl.
CPC .................................. *C07C 45/002* (2013.01)

(58) Field of Classification Search
USPC .................................................. 568/361, 376
See application file for complete search history.

(56) References Cited

U.S. PATENT DOCUMENTS

| | | | |
|---|---|---|---|
| 3,124,614 A | 3/1964 | Dankert | |
| 7,960,593 B2 * | 6/2011 | Gralla et al. | 568/830 |
| 2007/0191644 A1 | 8/2007 | Johann et al. | |
| 2013/0090496 A1 | 4/2013 | Schaub et al. | |
| 2013/0123526 A1 | 5/2013 | Schaub et al. | |
| 2013/0137893 A1 | 5/2013 | Ebel et al. | |
| 2013/0137901 A1 | 5/2013 | Strautmann et al. | |
| 2013/0172543 A1 | 7/2013 | Iwabuchi et al. | |
| 2013/0190532 A1 | 7/2013 | Schneider et al. | |
| 2013/0281696 A1 | 10/2013 | Schaub et al. | |
| 2013/0324770 A1 | 12/2013 | Schaub et al. | |
| 2013/0331532 A1 | 12/2013 | Porta Garcia et al. | |
| 2013/0331607 A1 | 12/2013 | Schaub et al. | |
| 2014/0024833 A1 | 1/2014 | Schelwies et al. | |
| 2014/0024854 A1 | 1/2014 | Schaub et al. | |

FOREIGN PATENT DOCUMENTS

| | | |
|---|---|---|
| DE | 4236111 A1 | 4/1994 |
| WO | WO-2005085160 A1 | 9/2005 |
| WO | WO-2012008228 A1 | 1/2012 |

OTHER PUBLICATIONS

Treibs, W., et al., "Ber der deutschen Chem. Ges.", vol. 60, No. 10, (1927), pp. 2335-2341.
U.S. Appl. No. 14/018,544.

* cited by examiner

*Primary Examiner* — Sikarl Witherspoon

(74) *Attorney, Agent, or Firm* — Drinker Biddle & Reath LLP

(57) ABSTRACT

The present invention relates to a method for preparing menthone, starting from isopulegol, using specific homogeneous catalysts.

14 Claims, 1 Drawing Sheet

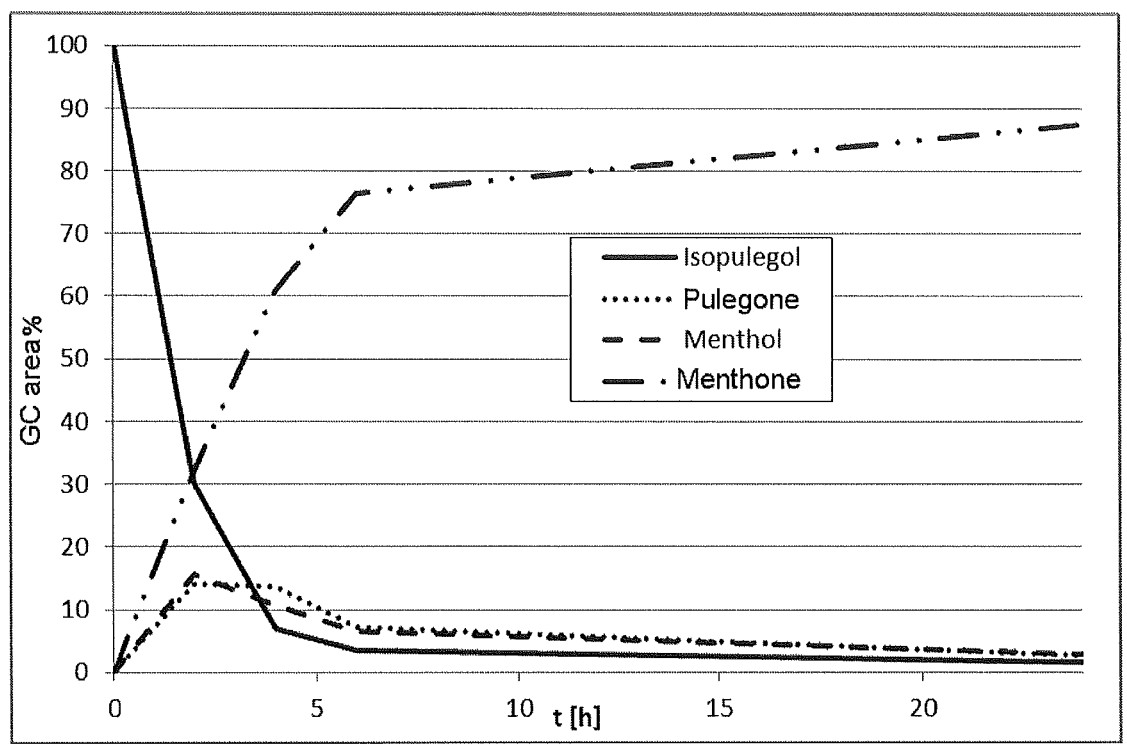

METHOD FOR PREPARING MENTHONE FROM ISOPULEGOL

CROSS-REFERENCE TO RELATED APPLICATIONS

This application claims the benefit of U.S. Provisional Application 61/698,745, filed Sep.10, 2012, which is incorporated herein by reference.

The present invention relates to a method for preparing menthone, starting from isopulegol, using specific homogeneous catalysts.

BACKGROUND TO THE INVENTION

Menthone exists in the form of two stereoisomers, menthone (I) and isomenthone (II), each of which in turn exists in the form of two enantiomers.

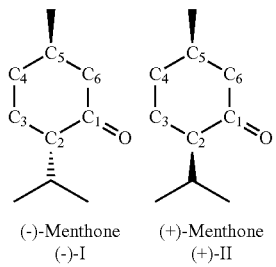

(-)-Menthone　　(+)-Menthone
(-)-I　　　　　　(+)-II

Both stereoisomers occur in various essential oils, particularly in oils of the species *Mentha*. Menthones exhibit a typically minty note, whereas isomenthones have a slightly musty odor. Industrial menthones are often mixtures of the isomers in varying compositions. Menthone and isomenthone are used for synthetic peppermint oils and peppermint bases (source: K. Bauer, D. Garbe, H. Surburg, Common Fragrance and Flavour Compounds, 4th Edition, Wiley-VCH).

Various methods for preparing menthone are known in the literature:

(-)-Menthone may be extracted by distillation from so-called dementholized cornmint oil, a residue from the isolation of (-)-menthol from the essential oil of wild or corn mint (*Mentha arvensis*). Dementholized cornmint oil comprises 30-50% of (-)-menthone (source: K. Bauer, D. Garbe, H. Surburg, Common Fragrance and Flavour Compounds, 4th Edition, Wiley-VCH). Due to the natural origin, menthone is, however, also subject to cyclical fluctuations leading to price fluctuations, exactly as in the case of menthol. Moreover, due to LD-production, a reduction in the proportion of (-)-menthol from natural sources also decreases the availability of the dementholized cornmint oil.

U.S. Pat. No. 3,124,614 describes the synthesis of menthone by hydrogenation of thymol in the presence of Pd/C catalysts. However, only a mixture of all stereoisomers is accessible by this route, i.e. a mixture of rac-menthone and rac-isomenthone. (-)-Menthone may also be prepared by oxidation of (-)-menthol. All established methods for the oxidation of secondary alcohols are possible here, for example oxidizing agents based on toxic heavy metals (e.g. chromic acid or dichromate/sulfuric acid) or else oxygen or air in the presence of a catalyst (e.g. N-oxyl compounds, WO 2012008228).

WO 2005/085160 A1 describes the preparation of menthone by dehydrogenation of menthol in the presence of a catalyst in the gas phase. In this manner, a mixture of menthone and isomenthone is obtained. The dehydrogenation of isopulegol to isopulegone is likewise mentioned, but not the conversion of isopulegone to menthone.

A similar gas phase dehydrogenation of menthol to menthone is also described in DE 4236111 A1.

A common feature of all these publications is that the preparation of menthone starts from menthol. In terms of atom economy, however, it would be better to prepare menthone starting from isopulegol.

The direct synthesis of menthone from isopulegol with copper catalysis in the gas phase is described by W. Treibs and H. Schmidt in *Berichte der Deutschen Chem. Gesellschaft* 1927, 60B, 2335-41. Under the conditions described therein, a considerable amount of thymol forms (35%). The menthone is obtained as an unspecified mixture of (-)-menthone and (+)-isomenthone. Nickel catalysts on the other hand, which may also be used for example for the dehydrogenation of menthol to menthone, lead to the elimination of water from the isopulegol.

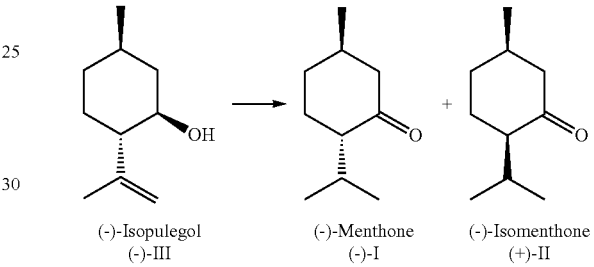

(-)-Isopulegol　　(-)-Menthone　　(-)-Isomenthone
(-)-III　　　　　(-)-I　　　　　　(+)-II

The problem to be addressed by the current invention is therefore to make available an improved method for preparing menthone.

OUTLINE OF THE INVENTION

The above problem has been solved according to the invention by a method in which menthone is obtained in high yields by hydrogenation/dehydrogenation under mild conditions starting from isopulegol.

The above problem has been solved in particular, according to the invention, by the following method described in detail for preparing menthone starting from isopulegol, which is carried out in a liquid phase using a homogeneously dissolved catalyst, comprising at least one element selected from groups 8, 9 and 10 of the periodic table.

The method according to the invention is characterized by the following advantages in comparison with the prior art:

Atom-economical preparation of menthone from isopulegol by dehydrogenation/hydrogenation, since all atoms of the reactant are still found in the product.

no racemization at position C-5.

considerably improved selectivities (up to 90%) compared to the closest prior art (W. Treibs and H. Schmidt in *Berichte der Deutschen Chem. Gesellschaft*, 35% selectivity) by using milder reaction conditions.

only traces of thymol are formed (<0.05%)

DESCRIPTION OF FIGURE

FIG. 1 shows a graphic representation of a representative reaction course according to the invention under the following experimental conditions: use of 20 g isopulegol, oil bath temperature 180° C., 0.3 mol % of [Ru(PnOct$_3$)$_4$(H)$_2$] catalyst, reaction under inert conditions in a glass flask with a reflux condenser; what is shown is the decrease of isopulegol with menthone formation and intermediate formation of menthol and isopulegone ("pulegone"); analysis by GC

DETAILED DESCRIPTION OF THE INVENTION a) Particular Embodiments of the Invention The present invention relates in particular to the following embodiments 1. A method for preparing menthone starting from isopulegol, wherein a rearrangement reaction is carried out, specifically a dehydrogenation/hydrogenation reaction, i.e. dehydrogenation of the OH group at the C1 atom to a keto group and a hydrogenation of the 1-methylethenyl group at the C2 atom of isopulegol, in the liquid phase using a homogeneously dissolved catalyst C, comprising at least one metal atom from group 8, 9 or 10, particularly 8 or 9, of the periodic table (IUPAC).

2. The method according to embodiment 1, wherein the catalyst C has ruthenium or iridium as the central atom M.

3. The method according to any of the previous embodiments, wherein the catalyst C comprises at least one phosphine ligand.

4. The method according to embodiment 3, wherein the catalyst C, in addition to having at least one phosphine ligand, has at least one further ligand L which is selected from the group consisting of CO, hydrido, aliphatic olefins, cyclic olefins, carbocyclic aromatic systems, heteroaromatic systems, aldehydes, ketones, halides, $C_1$-$C_4$-alkanoate, methylsulfonate, methylsulfate, trifluoromethylsulfate, tosylate, mesylate, cyanide, isocyanate, cyanate, thiocyanate, hydroxide, $C_1$-$C_4$-alkoxide, cyclopentadienide, pentamethylcyclopentadienide and pentabenzylcyclopentadienide.

Non-limiting examples
of aliphatic olefins are $C_2$-$C_4$-olefins, such as ethylene, propene, but-1-ene, but-2-ene, 2-methylprop-1-ene,
of cyclic olefins are cyclopropene, cyclobutene, cyclobutadiene, cyclopentadiene, cyclohexene, cyclohexadiene, cyclooctene, cyclooctadiene;
of carbocyclic aromatic compounds are benzene, naphthalene and anthracene, 1-isopropyl-4-methylbenzene, hexamethylbenzene,
of heteroaromatic compounds are pyridine, lutidine, picoline, pyrazine,
of aldehydes are formaldehyde, acetaldehyde, propionaldehyde, butyraldehyde, isobutyraldehyde, valeraldehyde, isovaleraldehyde, benzaldehyde, of ketones are acetone, menthone, of halides are F, Cl, Br, I,
of $C_1$-$C_4$-alkanoates are methanoate, ethanoate, n-propanoate and n-butanoate.

5. The method according to any of the previous embodiments, where the catalyst C is selected from among the compounds:
[Ru(PR$_3$)$_4$(H)$_2$] (R=methyl, ethyl, butyl, hexyl, octyl, phenyl, tolyl, mesityl),
[Ru(PR$_3$)$_3$(H)$_2$(CO)] (R=methyl, ethyl, butyl, hexyl, octyl, phenyl, tolyl, mesityl),
[Ru(PR$_3$)$_3$(H)(Cl)(CO)] (R=methyl, ethyl, butyl, hexyl, octyl, phenyl, tolyl, mesityl),
[Ru(PR$_3$)$_3$(Cl)$_2$(CO)] (R=methyl, ethyl, butyl, hexyl, octyl, phenyl, tolyl, mesityl),
[Ru(PR$_3$)$_3$(Cl)$_2$] (R=methyl, ethyl, butyl, hexyl, octyl, phenyl, tolyl, mesityl),
[Ru(L2)$_2$(H)$_2$] (L2=1,2-bisdicyclohexylphosphinoethane, 1,2-bisdiethylphosphinoethane, 1,2-bisdiphenylphosphinoethane),
[Ru(L2)(PR$_3$)$_2$(H)$_2$] (L2=1,2-bisdicyclohexylphosphinoethane, 1,2-bisdiethylphosphinoethane, 1,2-bisdiphenylphosphinoethane; R=methyl, ethyl, butyl, hexyl, octyl, phenyl, tolyl, mesityl),
[Ru(L2)(PR$_3$)(CO)(H)$_2$] (L2=1,2-bisdicyclohexylphosphinoethane, 1,2-bisdiethylphosphinoethane, 1,2-bisdiphenylphosphinoethane; R=methyl, ethyl, butyl, hexyl, octyl, phenyl, tolyl, mesityl),
[Ru(L2)(PR$_3$)(CO)(H)(Cl)] (L2=1,2-bisdicyclohexylphosphinoethane, 1,2-bisdiethylphosphinoethane, 1,2-bisdiphenylphosphinoethane; R=methyl, ethyl, butyl, hexyl, octyl, phenyl, tolyl, mesityl),
[Ru(L3)(H)$_2$] (L3=triphos), and
[Ru(L3)(CO)(H)$_2$] (L3=triphos),
and
[Ru(L3)(CO)(H)(Cl)] (L3=triphos)

6. The method according to any of the previous claims, wherein the catalyst C is used in an amount of 1 to 5000, 5 to 2000 or 10 to 1000 ppm parts by weight, based on 1 part by weight of isopulegol or of a mixture of one isopulegol with at least one different alcohol.

7. The method according to any of the previous embodiments, wherein an isomer mixture of isopulegol is used as starting compound.

8. The method according to any of the previous embodiments, wherein the product obtained is an isomer mixture of menthone.

9. The method according to any of the previous embodiments, wherein the reaction is carried out without additional solvent.

10. The method according to any of the preceding embodiments, wherein the reaction is carried out in the range from 100 to 250° C.

11. A reaction product obtainable by a method according to any of the previous embodiments.

12. The use of a reaction product according to embodiment 11 as a fragrance or flavouring.

13. A composition comprising at least one reaction product according to embodiment 11, wherein the composition is selected from foods, confectionery, chewing gum, beverages, cosmetics, toothpastes, mouth rinses, shampoos, toiletries, lotions, skincare products, medicaments and drugs.

b) Reactants

In the method according to the invention isopulegols and also mixtures of various isopulegols are used. Thus, (1R,2S,5R)-(−)-isopulegol, (1R,2S,5R)-(−)-isopulegol, (1S,2R,5R)-(+)-isopulegol, (1S,2R,5S)-(+)-isopulegol, (1S,2S,5R)-5-methyl-2-(1-methylethenyl)cyclohexanol or (1R,2R,5R)-5-methyl-2-(1-methylethenyl)cyclohexanol or mixtures of these isopulegols are used as isopulegols.

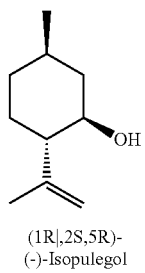

(1R|,2S,5R)-
(-)-Isopulegol

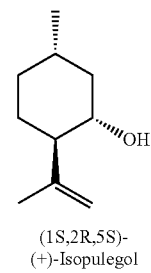

(1S,2R,5S)-
(+)-Isopulegol

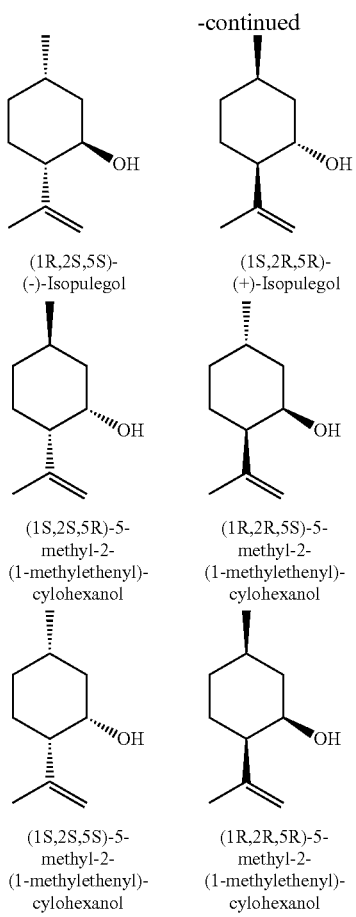

(1R,2S,5S)-
(-)-Isopulegol (1S,2R,5R)-
(+)-Isopulegol (1S,2S,5R)-5-
methyl-2-
(1-methylethenyl)-
cylohexanol (1R,2R,5S)-5-
methyl-2-
(1-methylethenyl)-
cylohexanol (1S,2S,5S)-5-
methyl-2-
(1-methylethenyl)-
cylohexanol (1R,2R,5R)-5-
methyl-2-
(1-methylethenyl)-
cylohexanol c) Catalyst Complexes In the method according to the invention at least one catalyst complex is used which comprises at least one element selected from groups 8, 9 and 10 of the periodic table (according to IUPAC nomenclature). The elements of group 8, 9 and 10 of the periodic table comprise iron, cobalt, nickel, ruthenium, rhodium, palladium, osmium, iridium and platinum. Preference is given to catalyst complexes which comprise at least one element selected from ruthenium and iridium. The active catalyst complex can be generated in its active form or else in situ from a simple metal precursor and a suitable ligand in the reaction mixture. Suitable metal precursors are, for example, [Ru(p-cymene)Cl$_2$]$_2$, [Ru(benzene)Cl$_2$]$_n$, [Ru(CO)$_2$Cl$_2$]$_n$, [Ru(CO)$_3$Cl$_2$]$_2$, [Ru(COD)(allyl)], [RuCl$_3$*H$_2$O], [Ru(acetylacetonate)$_3$], [Ru(DMSO)$_4$Cl$_2$], [Ru(cyclopentadienyl)(CO)$_2$Cl], [Ru(cyclopentadienyl)(CO)$_2$H], [Ru(cyclopentadienyl)(CO)$_2$]$_2$, [Ru(pentamethylcyclopentadienyl)(CO)$_2$Cl], [Ru(pentamethylcyclopentadienyl)(CO)$_2$H], [Ru(pentamethylcyclopentadienyl)(CO)$_2$]$_2$, [Ru(indenyl)(CO)$_2$Cl], [Ru(indenyl)(CO)$_2$H], [Ru(indenyl)(CO)$_2$]$_2$, ruthenocene, [Ru(COD)Cl$_2$]$_2$, [Ru(pentamethylcyclopentadienyl)(COD)Cl], [Ru$_3$(CO)$_{12}$], [IrCl$_3$*H$_2$O], KIrCl$_4$, K$_3$IrCl$_6$, [Ir(COD)Cl]$_2$, [Ir(cyclooctene)$_2$Cl]$_2$, [Ir(ethene)$_2$Cl]$_2$, [Ir(cyclopentadienyl)Cl$_2$]$_2$, [Ir(pentamethylcyclopentadienyl)Cl$_2$]$_2$ and [Ir(cyclopentadienyl)(CO)$_2$], [Ir(pentamethylcyclopentadienyl)(CO)$_2$].

The catalyst complex preferably comprises as ligand a phosphine ligand with at least one unbranched or branched, acyclic or cyclic, aliphatic or aromatic residue comprising 1 to 12 carbon atoms, where individual carbon atoms may also be replaced by >P—. In terms of branched cyclic aliphatic residues, also included here are residues such as —CH$_2$—C$_6$H$_{11}$, for example. Suitable residues are, for example, methyl, ethyl, prop-1-yl, prop-2-yl, but-1-yl, but-2-yl, 2-methylprop-1-yl, 2-methylprop-2-yl, pent-1-yl, hex-1-yl, hept-1-yl, oct-1-yl, non-1-yl, dec-1-yl, undec-1-yl, dodec-1-yl, cyclopentyl, cyclohexyl, cycloheptyl and cyclooctyl, methylcyclopentyl, methylcyclohexyl, 2-methylpent-1-yl, 2-ethylhex-1-yl, 2-propylhept-1-yl and norbonyl, phenyl, tolyl, mesityl and anisyl. The unbranched or branched, acyclic or cyclic, aliphatic or aromatic residue preferably comprises at least 1 and preferably a maximum of 10 carbon atoms. In the case of an exclusively cyclic residue in the abovementioned terms, the number of carbon atoms is 3 to 12 and preferably at least 4 and preferably a maximum of 8 carbon atoms. Preference is given to ethyl, but-1-yl, sec-butyl, oct-1-yl and cyclohexyl, phenyl, tolyl, mesityl and anisyl residues.

The phosphine group may comprise one, two or three of the abovementioned unbranched or branched, acyclic or cyclic, aliphatic or aromatic residues. These may be identical or different. The phosphine group preferably comprises three of the abovementioned unbranched or branched, acyclic or cyclic, aliphatic residues, with particular preference being given to all three residues being identical. Preference is given to phosphines P (n-C$_m$H$_{2n+1}$)$_3$ with m equal to 1 to 10, particularly preferably tri-n-butylphosphine, tri-n-octylphosphine, triphenylphosphine, diphenylphosphinoethane, chiraphos, triphos and 1,2-bis(dicyclohexylphosphino)ethane.

As already mentioned above, individual carbon atoms may also be replaced by >P— in the said unbranched or branched, acyclic or cyclic, aliphatic residues. Therefore, these also comprise polydentate, for example bi- or tridentate, phosphine ligands. These preferably comprise the

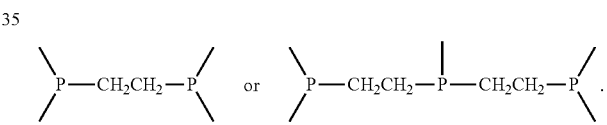

moiety.

If the phosphine group comprises still other residues than the abovementioned unbranched or branched, acyclic or cyclic, aliphatic residues, these generally correspond to those which are typically used elsewhere in phosphine ligands for organometallic catalyst complexes. Examples include phenyl, tolyl and xylyl.

The organometallic complex may comprise one or more, for example, two, three or four, of the abovementioned phosphine groups with at least one unbranched or branched, acyclic or cyclic, aliphatic or aromatic residue.

The catalyst complex may comprise still other residues, which could be unchanged ligands such as CO, olefins, cyclic olefins, dienes, cyclodienes, aromatic systems, aldehydes, ketones and anionic ligands such as fluoride, chloride, bromide, iodide, hydride, formate, acetate, propionate, butyrate, methylsulfonate, methylsulfate, trifluoromethylsulfate, tosylate, mesylate, cyanide, isocyanate, thiocyanate, hydroxide, alkoxide, cyclopentadienide, pentamethylcyclopentadienide and pentabenzylcyclopentadienide.

Preference is given to using catalysts of the type:

[Ru(PR$_3$)$_4$(H)$_2$] (R=methyl, ethyl, butyl, hexyl, octyl, phenyl, tolyl, mesityl),

[Ru(PR$_3$)$_3$(H)$_2$(CO)] (R=methyl, ethyl, butyl, hexyl, octyl, phenyl, tolyl, mesityl),

[Ru(PR$_3$)$_3$(H)(Cl)(CO)] (R=methyl, ethyl, butyl, hexyl, octyl, phenyl, tolyl, mesityl),

[Ru(PR$_3$)$_3$(Cl)$_2$(CO)] (R=methyl, ethyl, butyl, hexyl, octyl, phenyl, tolyl, mesityl),

[Ru(PR$_3$)$_3$(Cl)$_2$] (R=methyl, ethyl, butyl, hexyl, octyl, phenyl, tolyl, mesityl),

[Ru(L2)$_2$(H)$_2$] (L2=1,2-bisdicyclohexylphosphinoethane, 1,2-bisdiethylphosphinoethane, 1,2-bisdiphenylphosphinoethane),

[Ru(L2)(PR$_3$)$_2$(H)$_2$] (L2=1,2-bisdicyclohexylphosphinoethane, 1,2-bisdiethylphosphinoethane, 1,2-bisdiphenylphosphinoethane; R=methyl, ethyl, butyl, hexyl, octyl, phenyl, tolyl, mesityl),

[Ru(L2)(PR$_3$)(CO)(H)$_2$] (L2=1,2-bisdicyclohexylphosphinoethane, 1,2-bisdiethylphosphinoethane, 1,2-bisdiphenylphosphinoethane; R=methyl, ethyl, butyl, hexyl, octyl, phenyl, tolyl, mesityl),

[Ru(L2)(PR$_3$)(CO)(H)(Cl)] (L2=1,2-bisdicyclohexylphosphinoethane, 1,2-bisdiethylphosphinoethane, 1,2-bisdiphenylphosphinoethane; R=methyl, ethyl, butyl, hexyl, octyl, phenyl, tolyl, mesityl),

[Ru(L3)(H)$_2$] (L3=triphos),

[Ru(L3)(CO)(H)$_2$] (L3=triphos),

[Ru(L3)(CO)(H)(C)] (L3=triphos).

It can also be advantageous to add a base to the reaction mixture. Suitable bases are LiOH, NaOH, KOH, LiH, NaH, KH, Ca(OH)$_2$, CaH$_2$, LiAlH$_4$, NaBH$_4$, LiBH$_4$, Na$_2$CO$_3$, NaHCO$_3$, Li$_2$CO$_3$, LiHCO$_3$, K$_2$CO$_3$, KHCO$_3$, K$_3$PO$_4$, Na$_3$PO$_4$, BuLi, MeLi, PhLi, tBuLi, LiOMe, LiOEt, LiOPr, LiOiPr, LiOBu, LiOiBu, LiOPent, LiOiPent, LiOHex, LiOHept, LiOOct, LiOBenz, LiOPh, KOMe, KOEt, KOPr, KOiPr, KOBu, KOiBu, KOPent, KOiPent, KOHex, KOHept, KOOct, KOBenz, KOPh, NaOMe, NaOEt, NaOPr, NaOiPr, NaOBu, NaOiBu, NaOPent, NaOiPent, NaOHex, NaOHept, NaOOct, NaOBenz, NaOPh, KN(SiMe$_3$)$_2$, LiN(SiMe$_3$)$_3$, NaN(SiMe$_3$)$_3$, NH$_3$, RNH$_2$ (where R$_1$=unsubstituted or at least monosubstituted C$_1$-C$_{10}$-alkyl, H, (—C$_1$-C$_4$-alkyl-P(phenyl)$_2$), C$_3$-C$_{10}$-cycloalkyl, C$_3$-C$_{10}$-heterocyclyl comprising at least one heteroatom selected from N, O and S, C$_5$-C$_{14}$-aryl or C$_5$-C$_{10}$-heteroaryl comprising at least one heteroatom selected from N, O and S), R$_1$R$_2$NH (where R$_1$, R$_2$ independently of each other are unsubstituted or at least monosubstituted C$_1$-C$_{10}$-alkyl, H, (—C$_1$-C$_4$-alkyl-P(phenyl)$_2$), C$_3$-C$_{10}$-cycloalkyl, C$_3$-C$_{10}$-heterocyclyl comprising at least one heteroatom selected from N, O and S, C$_5$-C$_{14}$-aryl or C$_5$-C$_{10}$-heteroaryl comprising at least one heteroatom selected from N, O and S), R$_1$R$_2$R$_3$N (where R$_1$, R$_2$, R$_3$ independently of each other are unsubstituted or at least monosubstituted C$_1$-C$_{10}$-alkyl, H, (—C$_1$-C$_4$-alkyl-P(phenyl)$_2$), C$_3$-C$_{10}$-cycloalkyl, C$_3$-C$_{10}$-heterocyclyl comprising at least one heteroatom selected from N, O and S, C$_5$-C$_{14}$-aryl or C$_5$-C$_{10}$-heteroaryl comprising at least one heteroatom selected from N, O and S).

d) Rearrangement

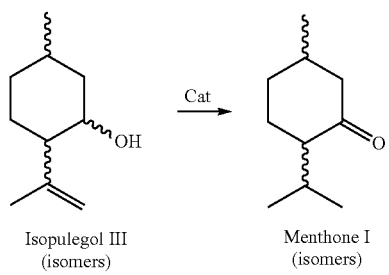

Isopulegol III (isomers)  Menthone I (isomers)

Menthone is formed from isopulegol by the dehydrogenation of the hydroxy group to a carbonyl function with hydrogenation of the C—C double bond of the substrate. Here a pure isomer of isopulegol and also an isomer mixture may be used. The menthone obtained from the reaction is a pure isomer or else is obtained as a mixture of isomers.

The reaction is carried out preferably with (−)-isopulegol, in which case (−)-menthone and (+)-isomenthon are formed as the main product.

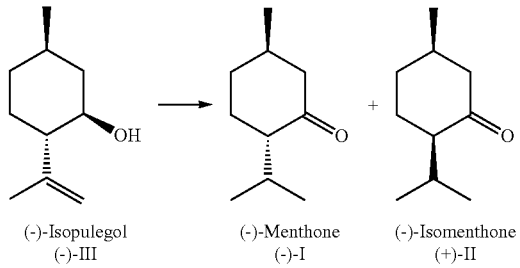

(−)-Isopulegol  (−)-Menthone  (−)-Isomenthone
(−)-III  (−)-I  (+)-II

In the context of the present invention, "homogeneously catalysed" is understood to mean that the catalytically active part of the catalyst complex is at least partly present dissolved in the liquid reaction medium. In a preferred embodiment, at least 90% of the catalyst complex used in the method is present dissolved in the liquid reaction medium, more preferably at least 95%, particularly preferably more than 99%, and most preferably the catalyst complex is present completely dissolved (100%) in the liquid reaction medium, based in each case on the total amount in the liquid reaction medium.

The amount of the metal component in the catalyst, preferably ruthenium, is generally 0.1 to 5000 ppm by weight, based respectively on the total liquid reaction mixture in the reaction space.

The reaction takes place in the liquid phase at a temperature of generally 20 to 250° C. The method according to the invention is preferably conducted at temperatures in the range from 100° C. to 200° C., particularly preferably in the range from 100 to 180° C.

The reaction is generally conducted at a total pressure of 0.1 to 20 MPa absolute, which can be either the autogenous pressure of the solvent or of the substrate at the reaction temperature or else the pressure of a gas such as nitrogen, argon or hydrogen. The method according to the invention is preferably conducted up to a total pressure of 10 MPa absolute, particularly preferably up to a total pressure of 1 MPa absolute.

In the method according to the invention, the reaction may be conducted either with an additional solvent or without solvent addition. Suitable solvents are, for example, aliphatic and aromatic hydrocarbons, aliphatic and aromatic ethers, cyclic ethers or esters. Examples include, but are not limited to, solvents such as pentane, hexane, heptane, octane, nonane, decane, benzene, toluene, xylenes, mesitylene, anisole, dibutyl ether, diphenyl ether, dimethoxyethane, tetrahydrofuran, methyltetrahydrofuran, dioxane, ethyl acetate, butyl acetate or butyl butyrate. If the reaction is conducted without additional solvent, then the product also does not have to be separated from it, which simplifies the workup. In the embodiment without solvent, the reaction takes place in the reactants and in the product formed in the reaction.

For the reaction in the liquid phase, at least one isopulegol and optionally the solvent, the metal catalyst or a suitable metal precursor, and the ligands, optionally with added base, are placed into a reaction space. The reaction may be conducted with the conventional apparatus and reactors for liquid-gas reactions known to a person skilled in the art, in which the catalyst is present dissolved homogeneously in the liquid phase. In principle, all reactors may be used in the method according to the invention which are basically suitable for gas-liquid reactions at the given temperature and the given pressure. Suitable standard reactors for gas-liquid and for liquid-liquid reaction systems are given, for example, in K. D. Henkel, "Reactor Types and Their Industrial Applications", in Ullmann's Encyclopedia of Industrial Chemistry, 2005, Wiley-VCH Verlag GmbH & Co. KGaA, DOI: 10.1002/14356007.b04_087, Chapter 3.3 "Reactors for gas-liquid reactions". Examples include stirred tank reactors, tubular reactors or bubble column reactors. The input of isopulegol and optionally the solvent, the metal catalyst or a suitable metal precursor and the ligands, optionally with an additional base, can take place simultaneously or separately from one another. The reaction may be conducted in a discontinuous batch mode, or continuously or semi-continuously with recycling or without recycling. The mean residence time in the reaction space is generally 15 minutes to 100 hours.

e) Purification

After the reaction, the product is separated, preferably by distillation, from unreacted reactants and optionally the solvent. The catalyst remains behind with the high boilers in the distillation bottoms and may be re-used. Unreacted alcohol reactant may likewise be recycled back into the reaction. The thermal separation of the alcohol and of the ester takes place according to the prior art methods known to a person skilled in the art, preferably in an evaporator or in a distillation unit, comprising evaporator and column(s), which typically has trays, a structured packing or a random packing. The separation of the product may also take place by crystallization, extraction or absorption, although workup by distillation is preferred.

Unreacted reactant and the metal catalyst are preferably re-used in the reaction to facilitate a highly economical process.

The invention is illustrated by, without being restricted to, the following examples:

EXPERIMENTAL SECTION

General Information:

The gas chromatographic determinations are carried out as follows: The GC determination of the yields was carried out with an Agilent system with a VF-23 ms column (60 m, 0.25 mm, 0.25 μm), helium as carrier gas and a flame ionization detector. The injector temperature was 250° C.; the column temperature was increased during the measurement from 50° C. to 150° C. with a heating rate of 3° C./min, and then to 260° C. at 20° C./min.

In the following examples the following definitions apply:
"Inert conditions": The procedures were conducted with exclusion of air and oxygen. The initial weighing of the reactant, solvent and catalyst took place in a glovebox, which is operated with purified nitrogen. The procedures outside the glovebox took place using standard Schlenk techniques and argon as inert gas.
"Normal pressure": atmospheric pressure, approximately 1 atmosphere
Yields: In the rearrangement of isopulegol to menthone, menthol and isopulegone occur as intermediates. With a longer reaction time or by recycling these intermediates, these can be further reacted to menthone, and thus do not constitute any loss of isopulegol with respect to the synthesis of menthone (see illustrative reaction course in the graph shown in FIG. 1 with respect to these components). These secondary components are explicitly mentioned in the yields and selectivity for this reason.

Preparation Example 1

Under inert conditions, 202 mg of $[Ru(PnOct_3)_4(H)_2]$, 1.8 g of isopulegol and 10 ml of o-xylene (anhydrous) are weighed out in a glovebox into a 50 ml two-necked flask. The reaction mixture is then stirred at normal pressure for 12 hours under reflux cooling at an oil bath temperature of 133° C. After the reaction, the conversion and the yield of menthone (sum of isomers) is determined by gas chromatography (Area %). The conversion of isopulegol is 60.5% with a selectivity for menthone (isomer mixture of 66.2% (−)-menthone, 33.8% (+)-isomenthone) of 47.3%. Selectivity for the secondary components: menthol 31.6%, isopulegone 14.9%, total selectivity (menthone+menthol+isopulegone) 93.8%.

Preparation Example 2

Under inert conditions, 116 mg of $[Ru(PnBu_3)_4(H)_2]$, 54 mg of 1,2-bis(dicyclohexylphosphino)ethane, 1.8 g of isopulegol and 10 ml of o-xylene (anhydrous) are weighed out in a glovebox into a 50 ml two-necked flask. The reaction mixture is then stirred at normal pressure for 12 hours under reflux cooling at an oil bath temperature of 133° C. After the reaction, the conversion and the yield of menthone (sum of isomers) is determined by gas chromatography (Area %). The conversion of isopulegol is 62.9% with a selectivity for menthone (isomer mixture of 61.7% (−)-menthone, 38.3% (+)-isomenthone) of 31.9%. Selectivity for the secondary components: menthol 27.7%, isopulegone 15.5%, total selectivity (menthone+menthol+isopulegone) 75.1%.

Preparation Example 3

Under inert conditions, 116 mg of $[Ru(PnEt_3)_4(H)_2]$, 1.8 g of isopulegol and 10 ml of o-xylene (anhydrous) are weighed out in a glovebox into a 50 ml two-necked flask. The reaction mixture is then stirred at normal pressure for 12 hours under reflux cooling at an oil bath temperature of 133° C. After the reaction, the conversion and the yield of menthone (sum of isomers) is determined by gas chromatography (Area %). The conversion of isopulegol is 64.2% with a selectivity for menthone (isomer mixture of 70.0% (−)-menthone, 33.0% (+)-isomenthone) of 45.2%. Selectivity for the secondary components: menthol 30.8%, isopulegone 20.2%, total selectivity (menthone+menthol+isopulegone) 96.2%.

Preparation Example 4

Under inert conditions, 404 mg of $[Ru(PnOct_3)_4(H)_2]$, 3.6 g of isopulegol and 10 ml of o-xylene (anhydrous) are weighed out in a glovebox into a 50 ml glass autoclave. The reaction mixture is then stirred under autogenous pressure (0.5 bar positive pressure) for 12 hours at an oil bath temperature of 130° C. After the reaction, the conversion and the yield of menthone (sum of isomers) is determined by gas chromatography (Area %). The conversion of isopulegol is 64.5% with a selectivity for menthone (isomer mixture of 65.8% (−)-menthone, 34.2% (+)-isomenthone) of 46.3%. Selectivity for the secondary components: menthol 30.2%, isopulegone 14.4%, total selectivity (menthone+menthol+isopulegone) 90.9%.

Preparation Example 5

Under inert conditions, 404 mg of [Ru(PnOct$_3$)$_4$(H)$_2$], 3.6 g of isopulegol and 20 ml of o-xylene (anhydrous) are weighed out in a glovebox into a 50 ml glass autoclave. The reaction mixture is then stirred under autogenous pressure for 12 hours at an oil bath temperature of 150° C. After the reaction, the conversion and the yield of menthone (sum of isomers) is determined by gas chromatography (Area %). The conversion of isopulegol is 92.4% with a selectivity for menthone (isomer mixture of 65.6% (−)-menthone, 34.4% (+)-isomenthone) of 51.1%. Selectivity for the secondary components: menthol 15.4%, isopulegone 10.9%, total selectivity (menthone+menthol+isopulegone) 77.4%.

Preparation Example 6

Under inert conditions, 460 mg of [Ru(PnOct$_3$)$_4$(H)$_2$], 8.6 g of isopulegol and 20 ml of o-xylene (anhydrous) are weighed out in a glovebox into a 50 ml glass autoclave. The reaction mixture is then stirred under autogenous pressure for 12 hours at an oil bath temperature of 170° C. After the reaction, the conversion and the yield of menthone (sum of isomers) is determined by gas chromatography (Area %). The conversion of isopulegol is 98.2% with a selectivity for menthone (isomer mixture of 65.4% (−)-menthone, 34.6% (+)-isomenthone) of 89.6%. Selectivity for the secondary components: menthol 3.6%, isopulegone 0.3%, total selectivity (menthone+menthol+isopulegone) 93.5%.

Preparation Example 7

Under inert conditions, 300 mg of [Ru(PnOct$_3$)$_4$(H)$_2$] and 21.0 g of isopulegol are weighed out in a glovebox into a 50 ml glass autoclave. The reaction mixture is then stirred under autogenous pressure for 100 hours at an oil bath temperature of 170° C. After the reaction, the conversion and the yield of menthone (sum of isomers) is determined by gas chromatography (Area %). The conversion of isopulegol is 99.3% with a selectivity for menthone (isomer mixture of 64.3% (−)-menthone, 35.7% (+)-isomenthone) of 86.4%. Selectivity for the secondary components: menthol 1.4%, isopulegone 4.9%, total selectivity (menthone+menthol+isopulegone) 92.7%.

Preparation Example 8

Under inert conditions, 610 mg of [Ru(PnOct$_3$)$_4$(H)$_2$] and 20.15 g of isopulegol are weighed out in a glovebox into a 100 ml glass flask. The reaction mixture is then stirred under reflux for 24 hours at an oil bath temperature of 170° C. After the reaction, the conversion and the yield of menthone (sum of isomers) is determined by gas chromatography (Area %). The conversion of isopulegol is 97.5% at a selectivity for menthone (isomer mixture of 63.1% (−)-menthone, 36.9% (+)-isomenthone) of 84.0%. Selectivity for the secondary components: menthol 5.1%, isopulegone 4.5%, total selectivity (menthone+menthol+isopulegone) 93.7%.

Preparation Example 9

Under inert conditions, 610 mg of [Ru(PnOct$_3$)$_4$(H)$_2$] and 20.7 g of isopulegol are weighed out in a glovebox into a 100 ml glass flask. The reaction mixture is then stirred under reflux for 24 hours at an oil bath temperature of 180° C. After the reaction, the conversion and the yield of menthone (sum of isomers) is determined by gas chromatography (Area %). The conversion of isopulegol is 98.5% at a selectivity for menthone (isomer mixture of 63.0% (−)-menthone, 37.0% (+)-isomenthone) of 88.7%. Selectivity for the secondary components: menthol 2.9%, isopulegone 2.7%, total selectivity (menthone+menthol+isopulegone) 94.3%.

The disclosure of the publications cited herein is expressly incorporated by way of reference.

The invention claimed is:

1. A method for preparing menthone starting from isopulegol, wherein a dehydrogenation/hydrogenation reaction is carried out in the liquid phase using a homogeneously dissolved catalyst C comprising at least one metal atom from group 8, 9 or 10 of the periodic table (IUPAC).

2. The method according to claim 1, wherein the catalyst C comprises ruthenium or iridium.

3. The method according to claim 1, wherein the catalyst C comprises at least one phosphine ligand.

4. The method according to claim 3, wherein the catalyst C, in addition to having at least one phosphine ligand, has at least one further ligand L which is selected from the group consisting of CO, hydrido, aliphatic olefins, cyclic olefins, carbocyclic aromatic systems, heteroaromatic systems, aldehydes, ketones, halides, $C_1$-$C_4$-alkanoate, methylsulfonate, methylsulfate, trifluoromethylsulfate, tosylate, mesylate, cyanide, isocyanate, cyanate, thiocyanate, hydroxide, $C_1$-$C_4$-alkoxide, cyclopentadienide, pentamethylcyclopentadienide and pentabenzylcyclopentadienide.

5. The method according to claim 1, wherein the catalyst C is selected from among the compounds:
   [Ru(PR$_3$)$_4$(H)$_2$] (R=methyl, ethyl, butyl, hexyl, octyl, phenyl, tolyl, mesityl),
   [Ru(PR$_3$)$_3$(H)$_2$(CO)] (R=methyl, ethyl, butyl, hexyl, octyl, phenyl, tolyl, mesityl),
   [Ru(PR$_3$)$_3$(H)(Cl)(CO)] (R=methyl, ethyl, butyl, hexyl, octyl, phenyl, tolyl, mesityl),
   [Ru(PR$_3$)$_3$(Cl)$_2$(CO)] (R=methyl, ethyl, butyl, hexyl, octyl, phenyl, tolyl, mesityl),
   [Ru(PR$_3$)$_3$(Cl)$_2$] (R=methyl, ethyl, butyl, hexyl, octyl, phenyl, tolyl, mesityl),
   [Ru(L2)$_2$(H)$_2$] (L2=1,2-bisdicyclohexylphosphinoethane, 1,2-bisdiethylphosphinoethane, 1,2-bisdiphenylphosphinoethane),
   [Ru(L2)(PR$_3$)$_2$(H)$_2$] (L2=1,2-bisdicyclohexylphosphinoethane, 1,2-bisdiethylphosphinoethane, 1,2-bisdiphenylphosphinoethane; R=methyl, ethyl, butyl, hexyl, octyl, phenyl, tolyl, mesityl),
   [Ru(L2)(PR$_3$)(CO)(H)$_2$] (L2=1,2-bisdicyclohexylphosphinoethane, 1,2-bisdiethylphosphinoethane, 1,2-bisdiphenylphosphinoethane; R=methyl, ethyl, butyl, hexyl, octyl, phenyl, tolyl, mesityl),
   [Ru(L2)(PR$_3$)(CO)(H)(Cl)] (L2=1,2-bisdicyclohexylphosphinoethane, 1,2-bisdiethylphosphinoethane, 1,2-bisdiphenylphosphinoethane; R=methyl, ethyl, butyl, hexyl, octyl, phenyl, tolyl, mesityl),
   [Ru(L3)(H)$_2$] (L3=triphos), and
   [Ru(L3)(CO)(H)$_2$] (L3=triphos), and
   [Ru(L3)(CO)(H)(Cl)] (L3=triphos).

6. The method according to claim 1, wherein the catalyst C is used in an amount of 1 to 5000 ppm parts by weight, based on 1 part by weight of isopulegol or of a mixture of one isopulegol with at least one different alcohol.

7. The method according to claim 1, wherein an isomer mixture of isopulegol is used as starting compound.

8. The method according to claim 1, wherein the product obtained is an isomer mixture of menthone.

9. The method according to claim 1, wherein the reaction is carried out without additional solvent.

10. The method according to claim 1, wherein the reaction is carried out in the range from 100 to 250° C.

11. A method for producing a fragrance or flavouring comprising:
   (a) preparing menthone by the process according to claim 1; and
   (b) introducing the menthone into a fragrance or flavouring composition.

12. A method for producing foods, confectionery, chewing gum, beverages, cosmetics, toothpastes, mouth rinses, shampoos, toiletries, lotions, skincare products, medicaments or drugs comprising:
   (a) preparing menthone by the process according to claim 1; and
   (b) introducing the menthone into a food, confectionery, chewing gum, beverage, cosmetic, toothpaste, mouth rinse, shampoo, toiletry, lotion, skincare product, medicament, or drug composition.

13. The method according to claim 1, wherein the catalyst C comprises at least one metal atom from group 8 or 9 of the Periodic Table of the Elements.

14. The method according to claim 1, wherein the catalyst C comprises ruthenium or iridium or rhodium.

\* \* \* \* \*